United States Patent
Staib et al.

(10) Patent No.: US 7,767,209 B2
(45) Date of Patent: Aug. 3, 2010

(54) MODIFIED VACCINIA VIRUS ANKARA (MVA) MUTANT AND USE THEREOF

(75) Inventors: Caroline Staib, Munich (DE); Gerd Sutter, Munich (DE); Sigried Kiesling, Munich (DE); Volker Erfle, Munich (DE)

(73) Assignee: GSF-Forschungszentrum fuer Umwelt und Gesundheit GmbH, Munich (DE)

( * ) Notice: Subject to any disclaimer, the term of this patent is extended or adjusted under 35 U.S.C. 154(b) by 0 days.

(21) Appl. No.: 11/375,159

(22) Filed: Mar. 14, 2006

(65) Prior Publication Data
US 2007/0160627 A1    Jul. 12, 2007

Related U.S. Application Data

(63) Continuation of application No. PCT/EP2004/010858, filed on Sep. 28, 2004.

(51) Int. Cl.
*A61K 39/285* (2006.01)
*C12N 7/01* (2006.01)
*C12N 7/02* (2006.01)
*C12N 15/863* (2006.01)
*C12N 15/39* (2006.01)

(52) U.S. Cl. .............. 424/199.1; 424/185.1; 424/232.1; 435/235.1; 435/239; 435/320.1

(58) Field of Classification Search ................... None
See application file for complete search history.

(56) References Cited

U.S. PATENT DOCUMENTS

2005/0019347 A1*   1/2005   Sutter et al. .............. 424/199.1

FOREIGN PATENT DOCUMENTS

| WO | WO 93/18153 | 9/1993 |
|---|---|---|
| WO | WO 97/02355 | 1/1997 |
| WO | WO 2005/030971 A1 | 4/2005 |

OTHER PUBLICATIONS

Spriggs, et al. Vaccinia and Cowpox Viruses Encode a Novel Secreted Interleukin-1-Binding Protein. Cell. 1992; 71:145-152.*
Staib, et al. Transient Host Reange Selection for Genetic Engineering of Modified Vaccinia Virus Ankara. BioTechniques. 2000; 28:1137-1148.*
Moss, et al. Host range restricted, non-replicating vaccinia virus vectors as vaccine candidates. Adv Exp Med Biol. 1996;397:7-13. Abstract Only.*
Blanchard, et al. Modified vaccinia virus Ankara undergoes limited replication in human cells and lacks several immunomodulatory proteins: Implications for use as a human vaccine. J Gen Virol. 1998; 79:1159-1167.*

(Continued)

*Primary Examiner*—Mary E Mosher
*Assistant Examiner*—Stuart W Snyder
(74) *Attorney, Agent, or Firm*—Jenkins, Wilson, Taylor & Hunt, P.A.

(57) ABSTRACT

The present invention is directed to a MVA mutant and its use in the immunotherapy and vaccination against numerous diseases, in particular in the prevention and therapy of cancer and infectious diseases.

15 Claims, 7 Drawing Sheets

OTHER PUBLICATIONS

Sutter, et al., A recombinant vector derived from the host range-restricted and highly attenuated MVA strain of vaccinia virus stimulates protective immunity in mice to influenza virus. Vaccine 1994; 12:1032-1040. Abstract Only.*

Trevor, et al. Transduction of human dendritic cells with a recombinant modified vaccinia Ankara virus encoding MUC1 and IL-2. Cancer Immunol Immunother. 2001; 50:397-407.*

Sutter, et al., A recombinant vector derived from the host range-restricted and highly attenuated MVA strain of vaccinia virus stimulates protective immunity in mice to influenza virus. Vaccine 1994; 12:1032-1040.*

Plebanski, et al. Protection from *Plasmodium berghei* infection by priming and boosting T cells to a single class I-restricted epitope with recombinant carriers suitable for human use.Eur J Immunol. 1998 28:4345-4355.*

Moss, et al. Host range restricted, non-replicating vaccinia virus vectors as vaccine candidates. Adv Exp Med Biol. 1996;397:7-13.*

International Search Report corresponding to PCT application No. PCT/EP2004/010858 dated Sep. 28, 2004.

Staib et al., "Transient host range selection for genetic engineering of modified vaccinia virus Ankara", *BioTechniques*, 28: 1137-1148, Jun. 2000.

Alcami et al., "A soluble receptor for interleuken-1β encoded by vaccinia virus: A novel mechanism of virus modulation of the host response to infection", *Cell*, 71: 153-167, Oct. 1992.

Spriggs et al., "Vaccinia and cowpox viruses encode a novel secreted interleukin-1-binding protein", *Cell*, 71: 145-152, Oct. 1992.

Kettle et al., "Vaccinia virus serpin B13R(SPI-2) inhibits interleukin-1β-converting enzyme and protects virus-infected cells from TNF- and Fas-mediated apoptosis, but does not prevent IL-1 β-induced fever", *Journal of General Virology*, 78: 677-685, 1997.

Alcami et al., "A mechanism for the inhibition of fever by a virus," Proc. Natl. Acad. Sci. USA, vol. 93, pp. 11029-11034 (1996).

Alcami et al., "A soluble receptor for Interleukin-1b encoded by vaccinia virus: a novel mechanism of virus modulation of the host response to infection," Cell, vol. 71, pp. 153-167 (1992).

Alcami, A., "Viral mimicry of cytokines, chemokines and their receptors," Nat. Rev. Immunol., vol. 3, pp. 36-50 (2003).

Antoine et al., "The complete genomic sequence of the modified vaccinia Ankara strain: comparison with other orthopoxviruses," Virology, vol. 244, pp. 365-396 (1998).

Belyakov et al., "Shared modes of protection against poxvirus infection by attenuated and conventional smallpox vaccine viruses," Proc. Natl. Acad. Sci. U S A, vol. 100, pp. 9458-9463 (2003).

Blanchard et al., "Future Vaccines for HIV," The Lancet, vol. 348, pp. 1741 (Dec. 1996).

Carroll et al., "Host range and cytopathogenicity of the highly attenuated MVA strain of vaccinia virus: propagation and generation of recombinant viruses in a nonhuman mammalian cell line," Virology, vol. 238, pp. 198-211 (1997).

Cosma et al., "Therapeutic vaccination with MVA-HIV-1 nef elicits Nef-specific T-helper cell responses in chronically HIV-1 infected individuals," Vaccine, vol. 22, pp. 21-29 (2003).

Drexler et al., "Highly attenuated modified vaccinia virus Ankara replicates in baby hamster kidney cells, a potential host for virus propagation, but not in various human transformed and primary cells," J. Gen. Virol., vol. 79, pp. 347-352 (1998).

Drexler et al., "Identification of vaccinia virus epitope-specific HLA-A*0201- restricted T cells and comparative analysis of smallpox vaccines," Proc. Natl. Acad. Sci. USA, vol. 100, pp. 217-222 (2003).

Hornemann et al., "Replication of modified vaccinia virus Ankara in primary chicken embryo fibroblasts requires expression of the interferon resistance gene E3L," J. Virol., vol. 77, pp. 8394-8407 (2003).

McConkey et al., "Enhanced T-cell immunogenicity of plasmid DNA vaccines boosted by recombinant modified vaccinia virus Ankara in humans," Nat. Med., vol. 9, pp. 729-735 (2003).

Meyer et al., "Mapping of deletions in the genome of the highly attenuated vaccinia virus MVA and their influence on virulence," J. Gen. Virol., vol. 72, pp. 1031-1038 (1991).

Morita et al., "Recombinant vaccinia virus LC16m0 or LC16m8 that expresses hepatitis B surface antigen while preserving the attenuation of the parental virus strain," Vaccine, vol. 5, pp. 65-70 (Mar. 1987).

Moss et al., "Immunology 101 at poxvirus U: Immune evasion genes," Semin. Immunol., vol. 13, pp. 59-66 (2001).

Rochlitz et al., "Phase I immunotherapy with a modified vaccinia virus (MVA) expressing human MUC1 as antigen-specific immunotherapy in patients with MUC1-positive advanced cancer," J. Gene Med., vol. 5, pp. 690-699 (2003).

Staib et al., "Improved host range selection for recombinant modified vaccinia virus Ankara," Biotechniques, vol. 34, pp. 694-696, 698, 700 (2003).

Staib et al., "Inactivation of the viral interleukin 1β receptor improves CD8+ T cell memory responses elicited upon immunization with modified vaccinia virus Ankara," J. Gen. Virol., vol. 86, Pt. 7, 1997-2006 (Jul. 2005).

Staib et al.,"Live viral vectors: vaccinia virus," Methods Mol. Med., vol. 87, pp. 51-68 (2003).

Sutter et al., "Nonreplicating vaccinia vector efficiently expresses recombinant genes," Proc. Natl. Acad. Sci. USA, vol. 89, pp. 10847-10851 (1992).

Sutter et al., "Novel vaccinia vector derived from the host range restricted and highly attenuated MVA strain of vaccinia virus," Dev. Biol. Stand., vol. 84, pp. 195-200 (1995).

Sutter et al., "Vaccinia Vectors as Candidate Vaccines: The Development of Modified Vaccinia Virus Ankara for Antigen Delivery," Current Drug Targets—Infectious Disorders, vol. 3, pp. 262-271 (2003).

* cited by examiner

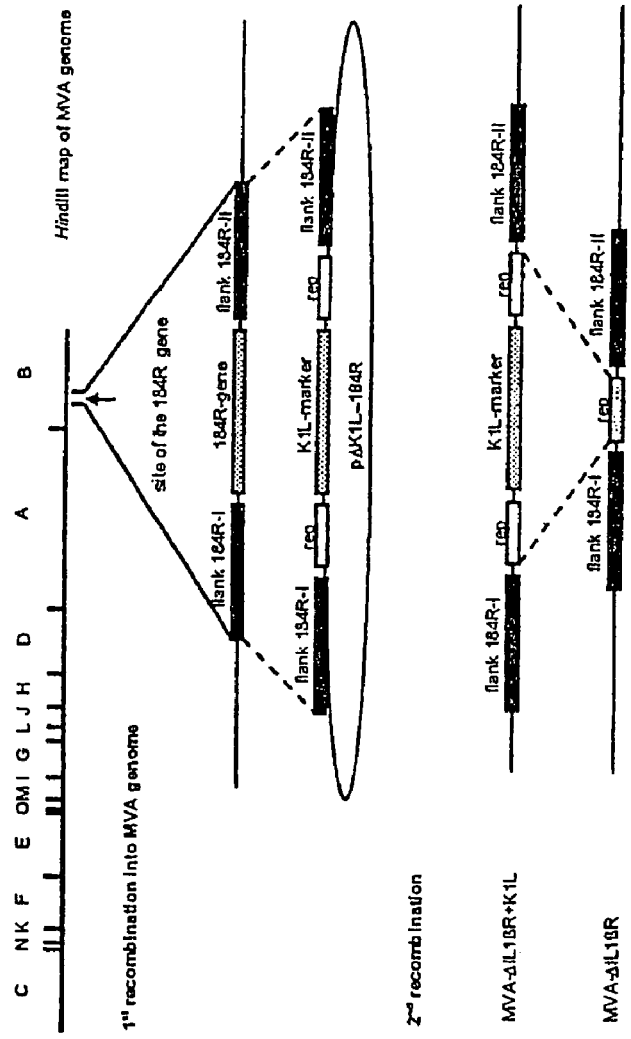
Figure 1, Staib et al.

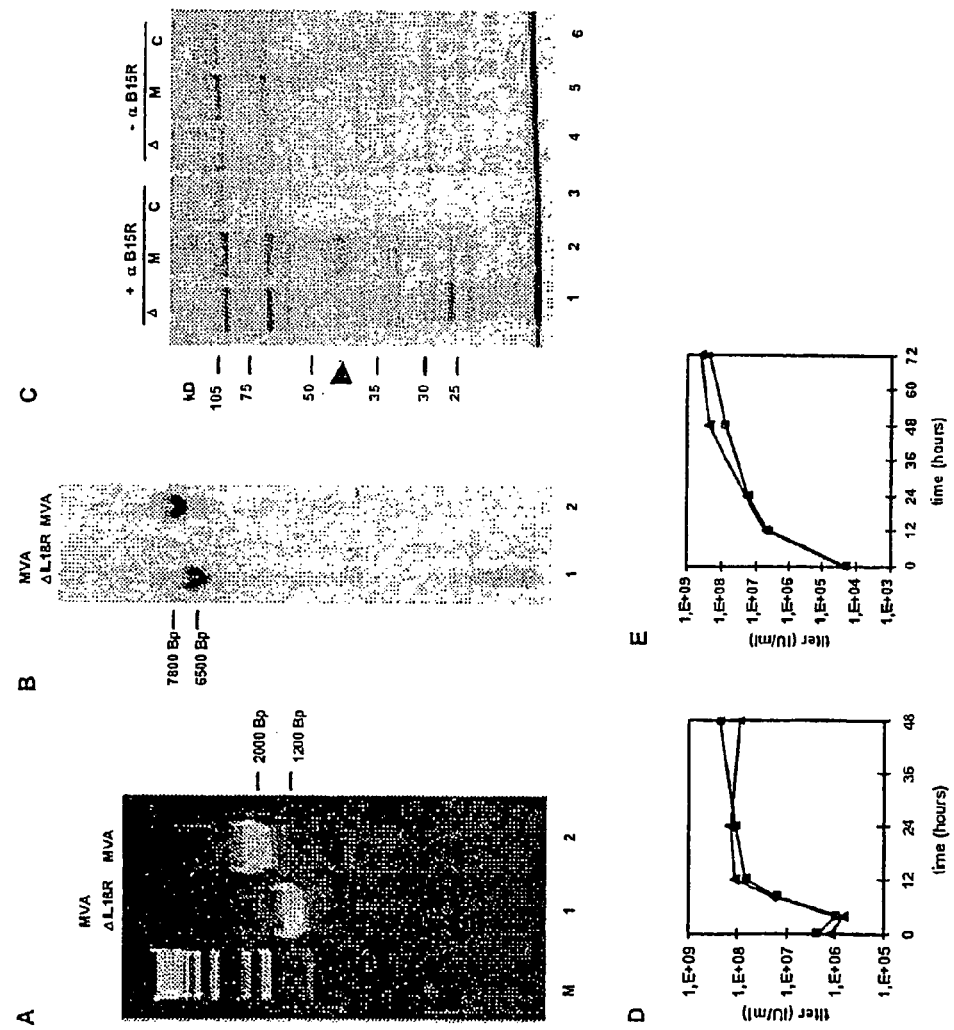
Figure 2, Staib et al.

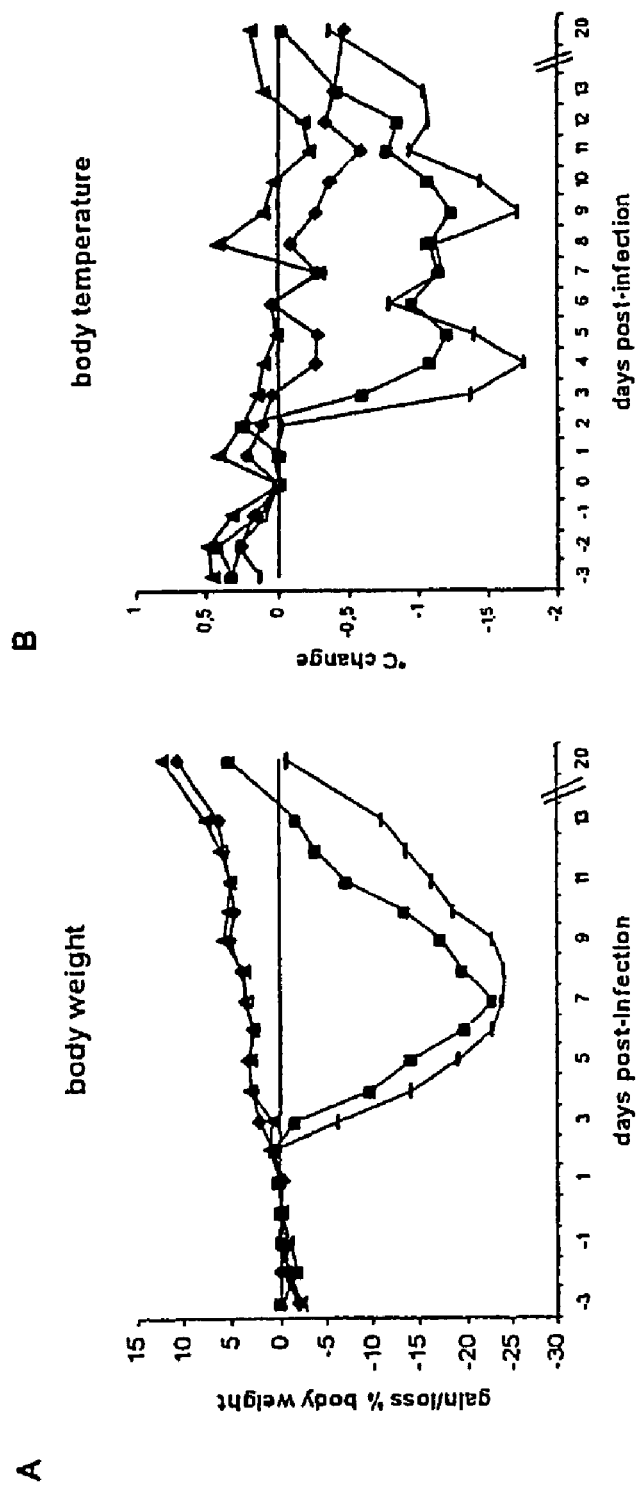
Figure 3, Staib et al.

Figure 4, Staib et al.

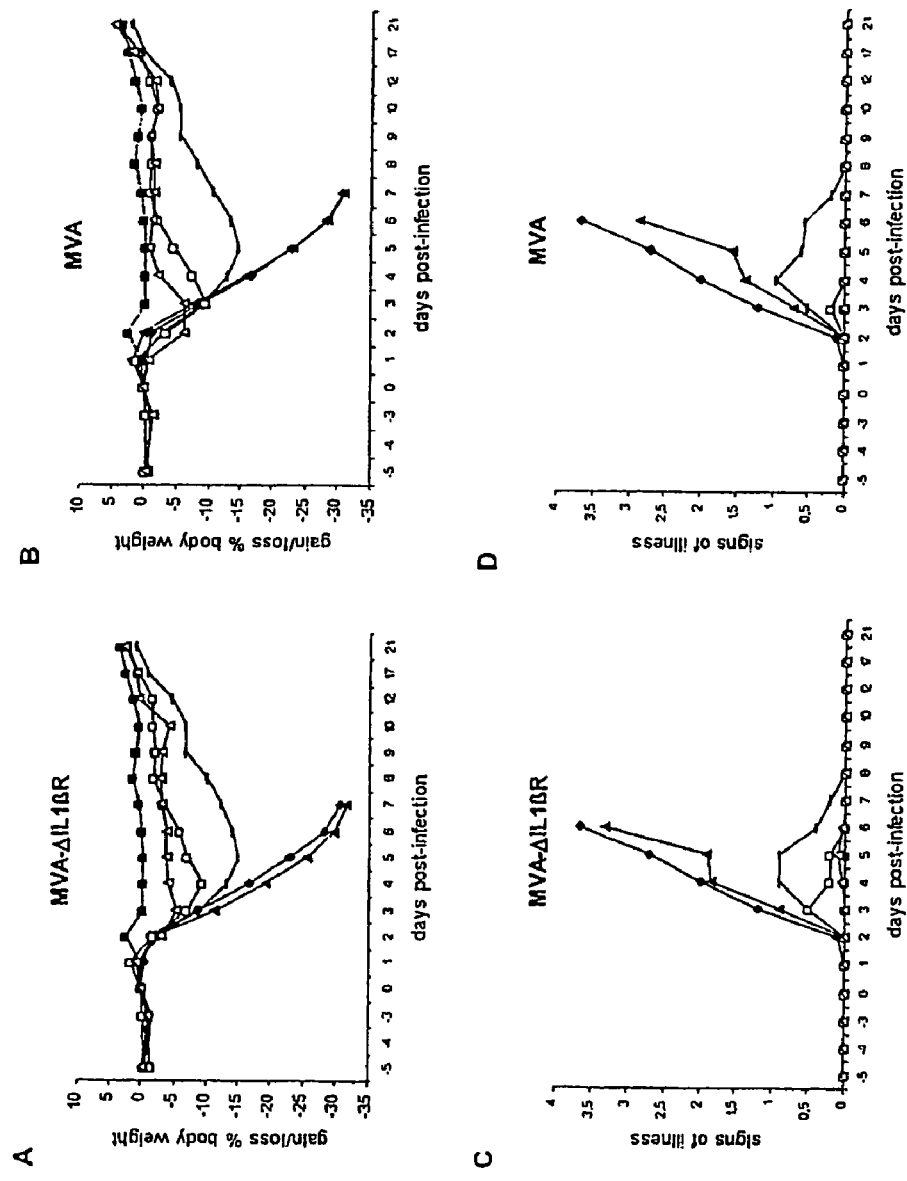
Figure 5, Staib et al.

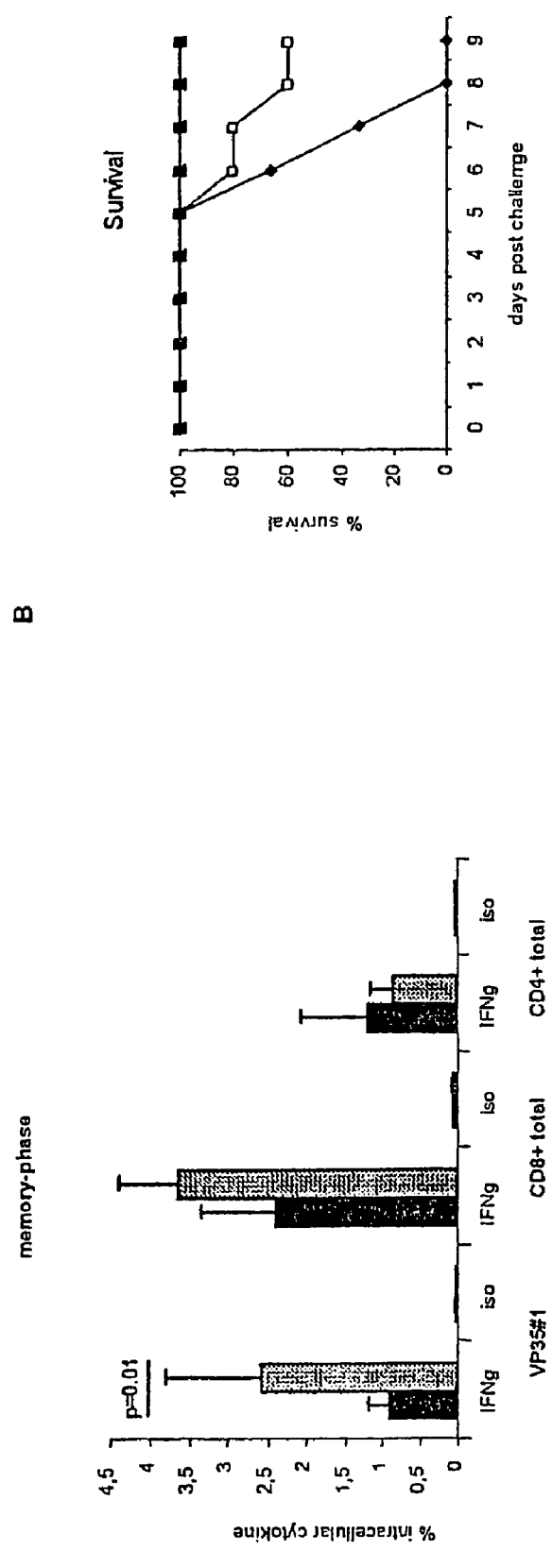
Figure 6, Stalb et al.

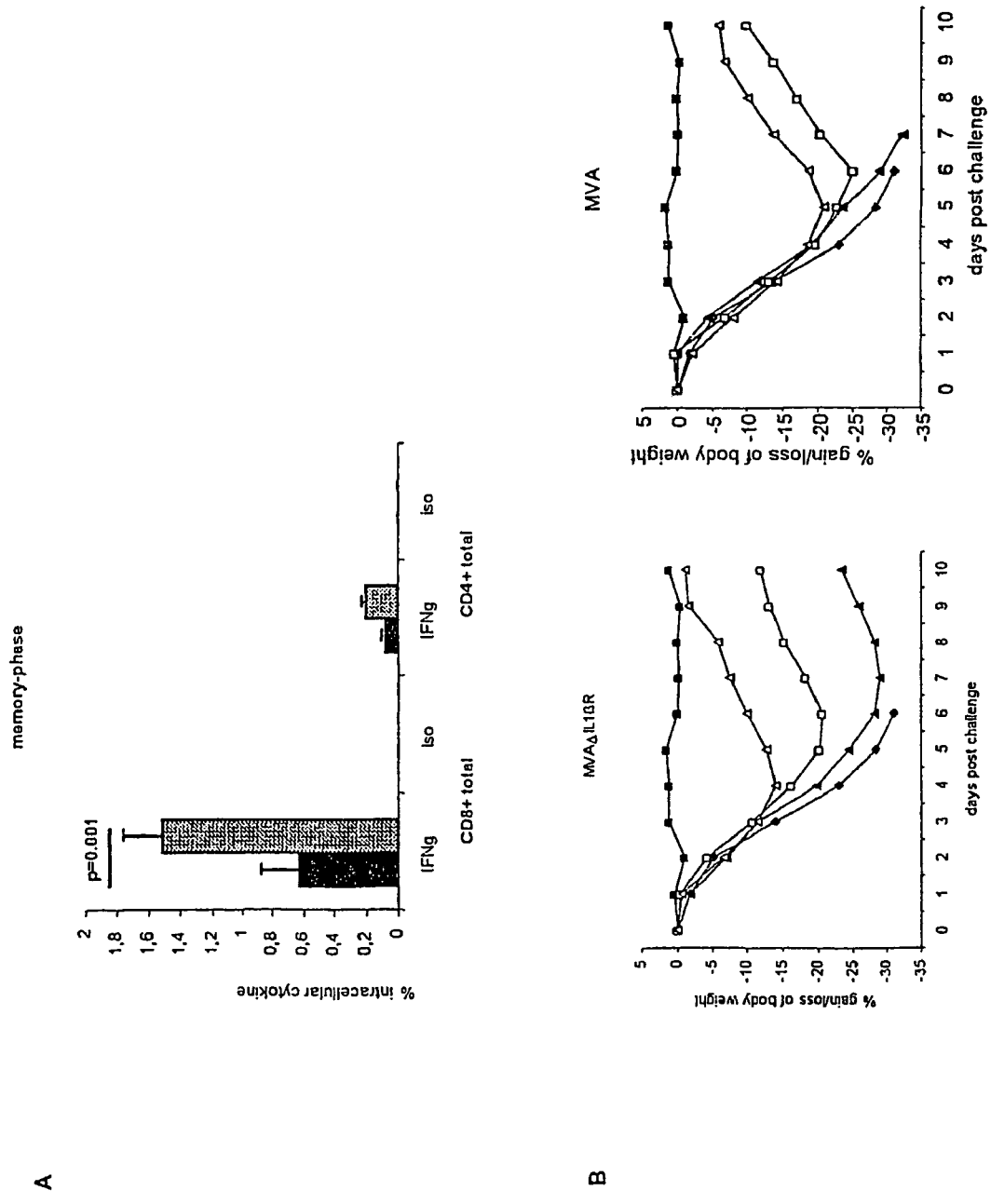
Figure 7, Staib et al.

MODIFIED VACCINIA VIRUS ANKARA (MVA) MUTANT AND USE THEREOF

RELATED APPLICATIONS

This application is a continuation of PCT International Patent Application No. PCT/EP2004/010858, filed Sep. 28, 2004, which claims priority to European Patent Application No. 03022112.1, filed Sep. 29, 2003, the disclosures of each of which are incorporated herein by reference in their entirety.

The present invention is directed to a MVA mutant and its use in the immunotherapy and vaccination against numerous diseases, in particular in the prevention and therapy of cancer and infectious diseases.

Vaccinia virus (VV) belongs to the genus Orthopoxvirus of the family of poxviruses. Certain strains of vaccinia virus have been used for many years as live vaccine to immunize against smallpox, for example the Elstree strain of the Lister Institute in the UK. Because of the complications which may derive from the vaccination (Schär, Zeitschr. für Präventivmedizin 18, 41-44 [1973]), and since the declaration in 1980 by the WHO that smallpox had been eradicated nowadays only people at high risk are vaccinated against smallpox.

Vaccinia viruses have also been used as vectors for production and delivery of foreign antigens (Smith et al., Biotechnology and Genetic Engineering Reviews 2, 383-407 [1984]). This entails DNA sequences (genes) which code for foreign antigens being introduced, with the aid of DNA recombination techniques, into the genome of the vaccinia viruses. If the gene is integrated at a site in the viral DNA which is non-essential for the life cycle of the virus, it is possible for the newly produced recombinant vaccinia virus to be infectious, that is to say able to infect foreign cells and thus to express the integrated DNA sequence (EP Patent Applications No. 83,286 and No. 110,385). The recombinant vaccinia viruses prepared in this way can be used, on the one hand, as live vaccines for the prophylaxis of infections, on the other hand, for the preparation of heterologous proteins in eukaryotic cells.

Vaccinia virus is amongst the most extensively evaluated live vectors and has particular features in support of its use as recombinant vaccine: It is highly stable, cheap to manufacture, easy to administer, and it can accommodate large amounts of foreign DNA. It has the advantage of inducing both antibody and cytotoxic responses, and allows presentation of antigens to the immune system in a more natural way, and it was successfully used as vector vaccine protecting against infectious diseases in a broad variety of animal models. Additionally, vaccinia vectors are extremely valuable research tools to analyze structure-function relationships of recombinant proteins, determine targets of humoral and cell-mediated immune responses, and investigate the type of immune defense needed to protect against a specific disease.

However, vaccinia virus is infectious for humans and its use as expression vector in the laboratory has been affected by safety concerns and regulations. Furthermore, possible future applications of recombinant vaccinia virus e.g. to generate recombinant proteins or recombinant viral particles for novel therapeutic or prophylactic approaches in humans, are hindered by the productive replication of the recombinant vaccinia vector. Most of the recombinant vaccinia viruses described in the literature are based on the Western Reserve (WR) strain of vaccinia virus. On the other hand, it is known that this strain is highly neurovirulent and is thus poorly suited for use in humans and animals (Morita et al., Vaccine 5, 65-70 [1987]).

Concerns with the safety of standard strains of W have been addressed by the development of vaccinia vectors from highly attenuated virus strains which are characterized by their restricted replicative capacity in vitro and their avirulence in vivo. Strains of viruses specially cultured to avoid undesired side effects have been known for a long time. Thus, it has been possible, by long-term serial passages of the Ankara strain of vaccinia virus (CVA) on chicken embryo fibroblasts, to culture a modified vaccinia virus Ankara (MVA) (for review see Mayr, A., Hochstein-Mintzel, V. and Stickl, H. (1975) Infection 3, 6-14; Swiss Patent No. 568 392). The MVA virus was deposited in compliance with the requirements of the Budapest Treaty at CNCM (Institut Pasteur, Collectione Nationale de Cultures de Microorganisms, 25, rue de Docteur Roux, 75724 Paris Cedex 15) on Dec. 15, 1987 under Depositary No. 1-721.

Modified vaccinia virus Ankara (MVA) is a chicken cell adapted strain of vaccinia virus. Because of its avirulence found upon inoculation of animals and its striking deficiency to produce substantial amounts of new viral progeny in most cells of mammalian origin MVA can be used under laboratory conditions of biosafety level 1. MVA serves as an efficient vector virus for expression of recombinant genes (Sutter & Moss 1992) and as candidate recombinant vaccine (Moss et al 1996) with high safety profile since MVA has been tested for preimmunization in over 100.000 humans being vaccinated against smallpox without causing notable side effects. Several MVA vector vaccines have already entered clinical evaluation (McConkey et al. 2003, Cosma et al. 2003). Most recently MVA is reassessed as candidate second generation vaccine against smallpox in comparison to immunizations with conventional vaccinia virus strains (Drexler et al. 2003, Belyakov et al. 2003).

As indicated above, MVA was obtained by long-term serial passage in chicken embryo fibroblast tissue cultures, which resulted in great loss of genomic information including many genes regulating virus-host interactions (Meyer et al. 1991, Antoine et al 1998). The MVA homologues of genes encoding recognized poxvirus immune evasion molecules (for review see Moss & Shisler 2001, Alcami 2003) including the viral interferon type I and type II receptors, the interleukin converting enzyme inhibitor SPI-2, the vaccinia complement binding protein, the vaccinia semaphorin, the 35 kDa chemokine binding protein or the tumor necrosis factor a receptor are deleted or fragmented. Interestingly, some viral genes with immunomodulatory function are maintained in the MVA genome and their possible relevance for the use of MVA-based vaccines remains to be determined. One such example is the coding sequence for the viral interleukin 1β receptor (IL1βR) that is highly conserved in MVA. Interleukin 1 is a cytokine that plays an important role in regulation of inflammatory processes and host innate immune response against infectious agents. In contrast to its cellular counterpart, the soluble viral IL1βR has specific affinity only for IL1β (Alcami & Smith Cell 1992), the major endogenous pyrogen (Alcami & Smith 1996). During vaccinia virus infection of mice IL1βR was shown to prevent fever by interaction with IL1β. Furthermore, deletion of the IL1βR gene in vaccinia virus accelerated the appearance of symptoms of illness and mortality in intranasally infected mice, suggesting that the blockade of IL1β by vaccinia virus can diminish the systemic acute phase response to infection and modulate the severity of the disease (Alcami & Smith 1996).

It is noted that a MVA mutant, in which the IL1βR gene has been inactivated, was already disclosed in Staib et al. in "Transient Host Range Selection for Genetic Engineering of Modified Vaccinia Virus Ankara", BioTechniques 28:1137-

1148 (June 2000). The deleted IL1βR gene sequence is termed and corresponds to ORF 184R. The whole genome of the MVA was disclosed in Antoine et al, Journal of Virology, 1998, which is incorporated herein by reference. However, no information was presented regarding the immunogenicity or further characteristics of the mutant, which could show their potential use in the prevention or therapy of numerous diseases.

As a summary, there remains a demand for an improvement of the already existing MVA strains in view of their immunogenicity and/or their protective capacities, when used as vaccines.

Therefore, one object underlying the present invention is to provide a MVA mutant, showing less unwanted immunoreactions and, at the same time, having superior immunogenicity in the long term treatment of several diseases.

This object is accomplished by the subject-matter of the independent claims. Preferred embodiments of the present invention are set forth in the dependent claims.

In this invention, the effects of the deletion of the IL1βR gene from the MVA genome are evaluated. The construction of MVA IL1βR deletion mutants allowed to analyze the significance of IL1βR synthesis upon in vitro and in vivo infection with MVA. The present data show that inactivation of the IL1βR gene is beneficial for the development of MVA vaccines.

Surprisingly, it turned out that an inactivation of the viral interleukin 1β receptor enhances CD8+ T cell responses elicited upon immunization with modified *vaccinia* virus Ankara.

Moreover, is could be shown herein that a MVA mutant lacking the IL1βR gene showed no signs of fever or other illness, also after a high dose intranasal infection of mice with MVA-ΔIL1βR. This fact was absolutely unexpected, since the deletion of the IL1βR gene in *vaccinia* virus (which was disclosed before, see above) accelerated the appearance of symptoms of illness and mortality in intranasally infected mice.

Interleukin-1 (IL1) is an important regulator of inflammatory and immune responses that contributes to host defense against infection. *Vaccinia* virus encodes a viral soluble IL1β receptor (vIL1βR), which modulates acute phase host response to infection (induction of fever) and might influence induction of immune responses against virus-associated antigens.

The inventors obtained MVA mutant viruses defective in vIL1βR production through transient insertion of selectable marker gene sequences, which precisely deleted the vIL1βR coding sequences from the MVA genome. Analysis of MVA mutants indicated that deletion of the vIL1βR gene did not abrogate the formation of MVA progeny upon tissue culture propagation. After high dose intranasal infection of mice with MVA-ΔIL1βR, animals showed no signs of fever or other illness suggesting that the avirulent phenotype remains preserved for MVA-ΔvIL1βR. Upon vaccination of mice MVA-ΔIL1βR or non-mutated MVA induced similar levels of *vaccinia* virus-specific circulating antibodies. Vaccination with MVA-ΔIL1βR elicited somewhat higher levels of *vaccinia* virus epitope-specific T cells. Yet, surprisingly a significantly superior immunogenicity of MVA-ΔIL1βR (p=0.01) was found when memory T cell responses were monitored at six months after vaccination. Moreover, while we found equal protective capacities for MVA-ΔIL1βR and wild-type MVA three weeks after immunization, at six months after vaccination MVA-ΔIL1βR protected better (5/5=100%, MVA 3/5=60%) against the lethal respiratory challenge with virulent *vaccinia* virus strain Western Reserve. Therefore, the data presented herein suggest that deletion of vIL1βR gene sequences may be considered as first step towards obtaining genetically optimized MVA viruses for the development of vaccines with even improved immunogenicity.

The present invention is in particular directed to the following aspects and embodiments:

The present invention is directed to a MVA mutant, wherein the IL1βR coding sequence or a functional part thereof has been inactivated, preferably by deletion or mutation, which mutant may be used in immunotherapy and/or vaccination.

The term "functional part thereof" as used herein is to be understood as any part of the IL1βR sequence, the loss of which is leading to an inactivation of the IL1βR function as described herein. The inactivation is preferably performed by mutation or deletion. This loss of function can, as mentioned above, be seen in the induction of immune responses against virus-associated antigens. Therefore, it does not require more than routine experimentation to determine for a skilled person, whether a certain deletion or mutation is capable of performing this or not. In particular, the immunological effect of enhancing CD8+ T cell responses may, for example, be evaluated by the method indicated in the Examples (see, in particular, FIG. 1) using a methodology as described in Tatsis N, Sinnathamby G, Eisenlohr LC; Methods Mol. Biol. 2004; 269:267-288.

In particular, any deletion or mutation of ORF184 will be regarded as being sufficient, which will lead to a memory response of CD8+ cells, which is enhanced by at least 10%, preferably at least 20%, more preferably 30 or 40% and most preferably more than 50% compared to unmodified, i.e. wild type, MVA.

Generally, the IL1βR gene or a functional part thereof can be inactivated by deletion from the viral genome. Alternatively, a recombinant MVA defective in IL1βR sequence function may be generated by sequence mutagenesis, e.g. insertional mutagenesis, leading to the inactivation of IL1βR.

The MVA mutant of the present invention may additionally comprise a foreign DNA sequence, which can be a gene coding for a therapeutic polypeptide, e.g secreted proteins, e.g. polypeptides of antibodies, chemokines, cytokines or interferons, or a polypeptide from a pathogenic agent which can be used preferably for vaccination purposes or for the production of therapeutic or scientific valuable polypeptides. Pathogenic agents are to be understood to be viruses, bacteria and parasites which may cause a disease, as well as tumor cells which multiply unrestrictedly in an organism and may thus lead to pathological growths. Examples of such pathogenic agents are described in Davis, B. D. et al., (Microbiology, 3rd ed., Harper International Edition). Preferred genes of pathogenic agents are those of influenza viruses, of measles and respiratory syncytial viruses, of dengue viruses, of human immunodeficiency viruses, for example HIV I and HIV II, of human hepatitis viruses, e.g. HCV and HBV, of herpes viruses, of papilloma viruses, of the malaria parasite *Plasmodium falciparum*, and of the tuberculosis-causing Mycobacteria.

Additionally, the MVA mutant of the present invention may be used for vaccination against smallpox or other diseases caused by orthopoxvirus infections.

Preferred genes encoding tumor associated antigens are those of melanoma-associated differentiation antigens, e.g. tyrosinase, tyrosinase-related proteins 1 and 2, of cancer testes antigens, e.g. MAGE-1,-2,-3, and BAGE, of non-mutated shared antigens overexpressed on tumors, e.g. Her-2/neu, MUC-1, and p53.

In order for it to be possible for the foreign DNA sequence or the gene to be expressed, it is necessary for regulatory sequences, which are required for the transcription of the gene, to be present on the DNA. Such regulatory sequences (called promoters) are known to those skilled in the art, for example a *vaccinia* virus specific promoter as that of the *vaccinia* 11 kDa gene as are described in EP-A-198,328, and those of the 7.5 kDa gene (EP-A-110,385) or a heterologous poxvirus promoter which allows for *vaccinia* virus specific transcription, or a synthetic promoter which allows for *vaccinia* virus specific transcription.

The ingredients of the present invention are preferably used in form of a pharmaceutical composition where they are mixed with suitable carriers or excipients in doses to treat or ameliorate the disease. Such a composition may also contain (in addition to the ingredient and the carrier) diluents, fillers, salts, buffers, stabilizers, solubilizers and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition may further contain other agents which either enhance the activity of the activity or use in treatment. Such additional factors and/or agents may be included in the pharmaceutical composition to produce a synergistic effect or to minimize side-effects.

Techniques for formulation and administration of the compounds of the instant application may be found in "Remington's Pharmaceutical Sciences", Mack Publishing Co., Easton, Pa., latest edition. Whenever the compositions are to be used for medical purposes, they will contain a therapeutically effective dose of the respective ingredient. A therapeutically effective dose further refers to that amount of the compound/ingredient sufficient to result in amelioration of symptoms, e.g., treatment, healing, prevention or amelioration of such conditions.

To prepare vaccines, the MVA *vaccinia* viruses generated according to the invention are converted into a physiologically acceptable form. This can be done based on the many years of experience in the preparation of vaccines used for vaccination against smallpox (Kaplan, Br. Med. Bull. 25, 131-135 [1969]). Typically, about $10^6$-$10^7$ particles of the recombinant MVA are freeze-dried in 100 ml of phosphate-buffered saline (PBS) in the presence of 2% peptone and 1% human albumin in an ampoule, preferably a glass ampoule. The lyophilisate can contain extenders (such as mannitol, dextran, sugar, glycine, lactose or polyvinylpyrrolidone) or other aids (such as antioxidants, stabilizers, etc.) suitable for parenteral administration. The glass ampoule is then sealed and can be stored, preferably at temperatures below −20° C., for several months.

For vaccination the lyophilisate can be dissolved in 0.1 to 0.2 ml of aqueous solution, preferably physiological saline, and administered parenterally, for example by intradermal inoculation. The vaccine according to the invention is preferably injected intracutaneously. Slight swelling and redness, sometimes also itching, may be found at the injection site (Stickl et al., supra). The mode of administration, the dose and the number of administrations can be optimized by those skilled in the art in a known manner. It is expedient where appropriate to administer the vaccine several times over a lengthy period in order to obtain a high level immune responses against the foreign antigen.

Thus, the MVA mutant of the present invention may be used in a method for treating a human patient in need of an immunotherapy and/or vaccination (which is, for example, suffering from cancer and/or infectious diseases), which is characterized in administering a therapeutically effective amount of a MVA mutant/vaccine of the invention to said patient. The physician in any event will determine the actual dosage which will be most suitable for an individual patient and will vary with the age, weight and response of the particular patient. There can, of course, be individual instances where higher or lower dosage ranges are merited, and such are within the scope of this invention.

Preferably, the pharmaceutical composition is adapted for in vivo use in a mammal, preferably a human patient.

According to a further aspect, a .method of generating mutant MVA is provided, comprising the steps of:
Infecting host cells of MVA with a nucleic acid coding for the MVA mutants as defined above,
expressing said nucleic acid under suitable conditions in said host cells; and
isolating expressed mutant MVA.

Furthermore, the present invention provides a method for generating a pharmaceutical composition comprising the steps of:
Infecting host cells of MVA with a nucleic acid coding for the MVA mutants as defined above,
expressing said nucleic acid under suitable conditions in said host cells;
isolating expressed mutant MVA;
adding a pharmaceutically acceptable carrier and further ingredients in order to manufacture a pharmaceutical composition.

According to a preferred embodiment, the host cells are CEF cells, chicken embryo derived LSCC-H32 cells, chicken DF-1 cells or avian cells, e.g. quail fibroblasts QT6 or QT35 cells.

Even more preferred, the mutant MVA are selected by the K1L gene based host range selection protocol (Staib et al., "Transient Host Range Selection For Genetic Engineering Of Modified *Vaccinia* Virus Ankara" BioTechniques 28: 1137-1148 (June 2000).

Compared to its parental strain, MVA has deletions that consist of about 15 percent (30,000 base pairs) of its former genome, including most of the K1L gene. Only a fragment of a length of 263 bp is still present in the MVA genome. The MVA K1L gene sequences represent the first 263 bp of the ORF 022L in the MVA genome at position nt 20685-20981 as described in Antoine, G., F. Scheiflinger, F. Dorner, and F. G. Falkner. 1998. The complete genomic sequence of the modified *vaccinia* Ankara strain and a comparison with other orthopoxviruses can be found in: Virology 244:365-396.

In Staib et aL, an easy and highly efficient method for generation of recombinant MVA based on selection for transient expression of the *vaccinia* virus host range gene K1L is described. This method is based on selection of recombinant MVA by transient host range gene expression using the *vaccinia* virus K1L gene function as stringent marker to rescue MVA growth on rabbit kidney RK-13 cells. The construction and use of new MVA vector plasmids was described which carry an expression cassette of the *vaccinia* virus host range gene K1L as transient selectable marker. These plasmids allow either stable insertion of additional recombinant genes into the MVA genome or precisely targeted mutagenesis of MVA genomic sequences. Repetitive DNA sequences flanking the K1L gene were designed to remove the marker gene from the viral genome by homologous recombination under non-selective growth conditions.

The publication of Straib et al., mentioned above, is incorporated herein in its entirety.

Additionally, the present invention provides the use of a MVA mutant as defined hereinabove or of a pharmaceutical composition, see above, for the manufacture of a medicament for use in immunotherapy and/or vaccination. Furthermore, the present invention is directed to a method for treating a patient, comprising a therapeutically effective dose of mutant MVA or of a pharmaceutical composition as defined herein to an individual in need of said treatment. Regarding the way and form of administration, see also above. The MVA mutant of the present invention may preferably used for vaccination against smallpox or other diseases caused by orthopoxvirus infections.

All publications, patent applications, patents, and other references mentioned herein are incorporated by reference in their entirety. In case of conflict, the present specification, including definitions, will control. In addition, the materials, methods, and examples are illustrative only and not intended to be limiting.

The present invention is further illustrated by the following figures.

BRIEF DESCRIPTION OF THE FIGURES

FIG. 1. Construction of IL1βR deficient MVA. Upper panel, schematic map of the MVA genome. Sites of the restriction endonuclease HindIII within the genome of MVA are indicated. The position of the 184R ORF (IL1βR gene) is marked by an arrow. MVA DNA sequences adjacent to the IL1βR coding sequence (flank 184R-I, flank 184R-II) were cloned into plasmid pΔK1L to allow for transient insertion of the K1L gene by homologous recombination at the site of ORF 184R, resulting in deletion of this gene sequence. The final mutant virus MVA-ΔIL1βR was obtained after the deletion of the K1L marker gene during a second step of homologous recombination involving synthetic repetitive sequences (rep).

FIG. 2. In vitro characterization of MVA-ΔIL1βR. (A) PCR analysis of viral DNA. Genomic template DNA was prepared from MVA-ΔIL1βR (lane 1) or MVA (lane 2) infected cells and incubated with oligonucleotides adjacent to the 184R gene locus to amplify specific DNA fragments. PCR products were separated by agarose gel electrophoresis. M, molecular weight marker. (B) Southern blot analysis of viral DNA. Genomic DNA was prepared from MVA-ΔIL1βR (lane 1) or MVA (lane2) infected cells, digested with EcoRI, separated by agarose gel electrophoresis and transferred to a nylon membrane. DNA fragments specific for the IL1βR gene locus were detected using a 32P-dCTP labeled specific probe. (C) Radioimmunoprecipitation of IL1βR proteins from lysates of MVA-ΔIL1βR (lanes 1, 4), MVA (lanes 2, 5) or mock (lanes 3, 6) infected and radiolabeled CEF cells. Immunoprecipitation was performed using polyclonal anti-B15R antibody coupled to Protein A (lanes 1-3) or uncoupled sepharose (lanes 4-6). The arrow head indicates the IL1βR protein. (D, E) Analysis of virus growth in CEF after high (D) or a low (E) MOI infection with MVA-ΔIL1βR (■) or MVA (▲).

FIG. 3. Analysis of virus virulence in a mouse model for respiratory poxvirus infection. Characterization of infections with MVA, MVA-ΔIL1βR, CVA, and WR. BALB/c mice (n=10) were inoculated by the intranasal route with 1×10$^8$ IU MVA (◆) and MVA-ΔIL1βR (▲), or 5×105 PFU CVA (■) and 3×104 PFU WR (-). Body weight (A) and body temperature (B) was monitored daily and is expressed as mean for each group.

FIG. 4 Ex vivo analysis of vaccine induced CD8+ T cells. HHD mice were vaccinated with a single dose of MVA-ΔIL1βR, MVA or a revertant virus. After 10 days, splenocytes were stimulated with the HLA-A*0201 resticted vaccinia specific VP35#1(VP35#1) or influenza M1 58-66 (irrelevant control) peptide, then stained with EMA, PE-anti-CD 8, APC-anti-CD62L and FITC-anti-IFNγ or -anti-TNFα or the respective FITC-labeled isotype control. Cells were analyzed by flow cytometry for the presence of VP35#1 peptide-specific, activated (CD62L$^{low}$) CD8+ T cells. The magnitude of the induced T cell response is depicted as percentages of cytokine secreting CD8+ T-cells within the live (EMA$^{negative}$) and CD8$^{positive}$ cell population. Representation of mean of 12 mice per group vaccinated with either MVA-ΔIL1βR (dark gray bars), MVA (solid black bars), or MVA-IL1βR-Rev (light gray bars), error bars indicate standard error x 1,96. p-value (p=0.07) was determined using Student's t-test.

FIG. 5 Analysis of vaccine-induced protection in a mouse model for respiratory poxvirus infection. BALB/c mice (n=10) were immunized intramuscularly with 10$^4$ (▲), 10$^5$ (-), 10$^6$ (□), 10$^7$ (Δ) IU of MVA-ΔIL1βR (A, C) or MVA (B, D). Three weeks after vaccination animals were challenged intranasally with 1×10$^6$ PFU WR. Individual animal weights (A, B) and signs of illness (C, D) were monitored daily and are expressed as means for each group. Mock vaccinated (◆) and mock challenged (■) mice served as control groups.

FIG. 6 Ex vivo analysis of vaccine induced memory CD8+ T cells and analysis of vaccine-induced long-term protection in HHD mice. (A) Mice were vaccinated intraperitoneally with a single dose 10$^8$ IU of MVA-ΔIL1βR or MVA. After 6 month, splenocytes were either stimulated with the HLA-A*0201 restricted vaccinia specific VP35#1 peptide or infected with MVA for detection of vaccinia specific total CD8+ or CD4+ responses. Cells were stained with EMA, PE-anti-CD8, APC-anti-CD62L and FITC-anti-IFNγ or the respective FITC-labeled isotype control. Cells were analyzed by flow cytometry for the presence of VP35#1peptide or vaccinia-specific, activated (CD62L$^{low}$) CD8+ T cells or vaccinia specific CD4+ T cells. The mean of 6 mice is depicted after vaccination with either MVA-ΔIL1βR (dark gray bars) or MVA (solid black bars), error bars indicate standard error x 1.96. p-value (p=0.01) was determined using Student's t-test. (B) HHD mice (n=5) were immunized intraperitoneally with 10$^8$ IU of MVA-ΔIL1βR (Δ) or MVA (□). At 6 month after vaccination mice were challenged with 1×10$^7$ PFU WR. Survival was monitored daily and is expressed as percentage of surviving animals per group. Mock vaccinated (◆) and mock challenged (■) mice served as control groups. In FIG. 6B, the mock challenged (■) mice and mice immunized intraperitoneally with 10$^8$ IU of MVA-ΔIL1βR (Δ) remained at 100%, thereby causing the symbols (■) and (Δ) to overlap in the graph.

FIG. 7 Ex vivo analysis of vaccine induced memory CD8+ T cells and analysis of vaccine-induced long-term protection in non transgenic mice. (A) C57BL/6 mice were vaccinated intraperitoneally with a single dose 10$^8$ IU of MVA-ΔIL1βR or MVA. After 6 month, splenocytes were infected with MVA for detection of vaccinia specific total CD8+ or CD4+ responses. Cells were stained with EMA, PE-anti-CD8, APC-anti-CD62L and FITC-anti-IFNγ or the respective FITC-labeled isotype control. Cells were analyzed by flow cytometry for the presence of vaccinia-specific, activated (CD62L$^{low}$) CD8+ T cells or vaccinia specific CD4+ T cells. The mean of 6 mice is depicted after vaccination with either MVA-ΔIL1βR (dark gray bars) or MVA (solid black bars), error bars indicate standard error x 1.96. p-value (p=0.001) was determined using Student's t-test. (B) BALB/c mice (n=4) were immunized intranasally with 10$^5$ (▲), 10$^6$ (□) or 10$^7$ (Δ) IU of MVA-ΔIL1βR or MVA. 4 month after vaccination animals were challenged intranasally with 1×10$^7$ PFU WR. Individual animal weights were monitored daily and are expressed as means for each group. Mock vaccinated (♦) and mock challenged (■) mice served as control groups.

The following example is intended to contribute to a better understanding of the present invention. However, it is not intended to give the impression that the invention is confined to the subject-matter of the example.

Materials and Methods

Viruses and cells. *Vaccinia* virus strains Western Reserve, CVA and MVA (cloned isolate F6, from the 582$^{nd}$ passage on chicken embryo fibroblasts (CEF)) were used for this study. All viruses were propagated and titered following standard methodology. To generate vaccine preparations, viruses were routinely purified by ultra centrifugation through sucrose and reconstituted in 1 mM Tris pH 9.0. CEF and rabbit kidney RK-13 (ATCC CCL-37) cells were grown in minimal essential medium (MEM) supplemented with 10% fetal calf serum (FCS), and maintained at 37° C. and 5% $CO_2$.

Plasmids. The transfer plasmid pΔK1L-184R carries two DNA fragments that represent flanking sequences of MVA ORF 184R (nucleotide position 162021-163001, GenBank U94848) and which were inserted into multiple cloning sites 1 and 2 of plasmid pΔK1L (Staib et al. 2000). One fragment, designated flank184-1, consists of a 486-bp MVA-DNA sequence starting in the 5' intergenic region of ORF 184R and ending at the start codon for translation of ORF 184R, the other fragment, flank184-2, is a 544-bp PCR-fragment of MVA-DNA extending from the codon for 184R translation termination into the 3'-intergenic region of the 184R gene.

Genetical modification of *vaccinia* virus MVA. Mutant MVA were obtained following the transient K1L-based host range selection protocol as described previously (Staib et al, 2000). Briefly, for generation of deletion mutant viruses, monolayers of $1 \times 10^6$ confluent CEF cells were infected with MVA at a multiplicity of infection (MOI) of 0.01 IU per cell. Ninety minutes after infection cells were transfected with 1.5 µg of plasmid pΔK1L-184R DNA using FUGENE™ (Roche, Mannheim, Germany) as recommended by the manufacturer. At 48 h after infection, transfected cells were harvested and plated on RK-13 cell monolayers for growth selection. Mutant viruses were isolated through plaque cloning on RK-13 cells and then passaged on CEF cells to remove the selectable marker gene K1L.

Analysis of viral DNA by PCR and Southern blot. Genomic viral DNA was isolated from infected CEF cells and analyzed by PCR using oligonucleotides annealing within the flanking regions flank184-1 and -2, respectively (pair 1) or within flank184-1 and the coding region of 184R, respectively (pair 2) (Staib et al., 2000). Specific DNA fragments were amplified by 30 cycles of PCR at an annealing temperature of 52° C. (pair 1) or 50° C. (pair 2).

Alternatively, total DNA isolated from virus-infected cells was digested with EcoRI, separated by gel electrophoresis in 0.8% agarose, transferred to a Hybond TM-N membrane (Amersham, Freiburg, Germany), and hybridized to a DNA probe consisting of a PCR fragment from 184R-flank1 sequences labeled with [α-$^{32}$P]CTP. Prehybridization and hybridization was performed according to Sambrook et al. (Southern 1975, Sambrook et al., 1989). Blots were exposed to a Kodak BioMax film.

Radioimmunoprecipitation of virus-infected cell lysates. CEF cells grown in 6-well tissue culture plates were infected with a multiplicity of 20 infectious units MVA. At 2 h post infection, the virus inoculum was replaced with methionine-free minimal essential medium containing 5% dialyzed fetal calf serum and 50 µCi of [$^{35}$S]methionine per ml and incubated overnight at 37° C. Cells were lysed in RIPA-buffer containing 0.15 M NaCl, 0.01 M Tris-HCl (pH 7.4), 1% Triton X-100, and incubated for 14 h with rabbit polyclonal antibody AcB15R (Alcami & Smith, 1992), followed by 50% protein A-sepharose suspension. Immune complexes were washed in RIPA-buffer, resuspended in Laemmli buffer, and proteins were separated by electrophoresis in a 10% SDS-polyacrylamide gel.

Analysis of virus growth. To determine low or high multiplicity growth profiles, confluent CEF monolayers (grown on 6 well plates) were infected with 0.05 infectious units (IU) or 10 IU MVA or mutant MVA per cell, respectively. After virus adsorption for 60 min at 37° C., the inoculum was removed. Cells were washed twice with RPMI 1640 and incubated with fresh RPMI 1640 medium containing 10% FCS at 37° C. and 5% $CO_2$. At multiple time points post infection (p.i.) infected cells were harvested and virus was released by freeze-thawing and brief sonication. Serial dilutions of the resulting lysates were plated on confluent CEF monolayers grown in 6-well plates as replicates of two. 48 hours p.i., monolayers were briefly fixed in acetone:methanol (1:1), and cells were incubated for 60 min with polyclonal rabbit anti-*vaccinia* antibody (IgG fraction, Biogenesis Ltd, Poole, England, Cat.No. 9503-2000, diluted 1:1000 in PBS-3% FCS), followed by an incubation for 45 min with horseradish-peroxidase-conjugated polyclonal goat anti-rabbit antibody (Dianova, Hamburg, Germany, dilution 1:1000 in PBS-3% FCS). After washing with PBS, antibody-labeled cells were developed using o-dianisidine (Sigma, Taufkirchen, Germany) substrate solution, foci of stained cells were counted, and virus titers were calculated as IU/ml.

Humoral *vaccinia* virus responses. Serum samples from mice immunized with MVA, mutant MVA, or *vaccinia* virus CVA were assessed for antibodies to *vaccinia* virus proteins by ELISA and neutralizing-antibody assay. *Vaccinia* antigen-specific binding titers were determined by an ELISA in which Maxisorp plates (Nunc, Germany) were coated with sucrose-gradient purified MVA (at a protein concentration of 1 µg/ml) for 3 h at 37° C. and overnight at 4° C. Plates were blocked with PBS/0.05% Tween 20/10% fetal calf serum for 60 min at 37° C. Serial dilutions of serum samples were incubated for 60 min at 37° C., washed five times with PBS, and incubated for 30 min with anti-mouse alkaline-phosphatase conjugate (diluted 1:1000 in PBS). Following five washes, plates were incubated with pNPP substrate (Sigma, Germany) at 37° C., after 20 min, the optical density was measured on an ELISA reader at a wavelength of 405 nm.

*Vaccinia* virus-specific neutralizing antibodies were analyzed by a plaque reduction assay using recombinant MVA-LZ. Twofold serial dilutions of sera were mixed with 200 infectious units MVA-LZ in a total volume of 200 µl PBS and incubated for two hours at 37° C. Afterwards, confluent CEF monolayers (grown on 24 well plates) were infected in duplicate, and foci of virus infected cells were visualized 48 hours after inoculation by staining with 5-bromo-4-chloro-3-indolyl-β-galactopyranoside substrate (X-Gal, Roche Molecular Biochemicals, Mannheim Germany) as described previously (Drexler et al., 1998). Blue-stained foci were counted and the number obtained with each serum was compared to controls with mouse preimmune sera or medium control. Antibody titers were calculated as the serial twofold dilution yielding a 50% reduction of foci numbers.

Cellular *vaccinia* virus responses. For monitoring of peptide-specific acute and memory phase CD8+ T cell responses, splenocytes from *vaccinia* virus-immunized HHD mice were prepared and incubated for 5 h with A*0201-binding peptides at $10^{-6}$ M. After 2 h, brefeldin A was added at a final concentration of 1 µg/ml (Golgiplug™; PharMingen Becton Dickinson). Cells were then either stored ON on ice at 4° C., or directly live/dead stained in PBS/1% BSA/1 µg/ml ethidium monoazide bromide (EMA; Molecular Probes) and blocked for unspecific FcγIII and -II receptor-mediated binding with 5 µg/ml purified anti-CD16/CD32 (Fc Block™; PharMingen Becton Dickinson) for 20 min at 4° C. Cell surface staining was performed with PE-anti-CD8 (53-6.7) and APC-anti-CD62L (Mel-14) for 30 min at 4° C. After permeabilization of cells (Cytofix/Cytoperm™ Kit, PharMingen Becton Dickinson), intracellular cytokine staining was performed for 30 min at 4° C. applying FITC-anti-IFNγ (XMG1.2) or FITC-anti-TNFα (MP6-XT22) or the respective FITC-labeled IgG1 isotype control (R3-34) (all PharMingen Becton Dickinson). Splenocytes were analyzed by four-color flow cytometry (FACSCalibur™) using CellQest® software (both Becton Dickinson).

Animal models. Female six to eight week-old transgenic HHD$^{+/+}$ β$_2$m$^{-/-}$ D$^{b-/-}$ mice (HHD) (Pascolo et al., 1997) or female six to eight week old BALB/c or C57BL/6 mice were used for vaccination experiments. HHD mice were inoculated with 0.5 ml volumes of virus vaccine by the intraperitoneal route, and monitored for HLA-A*0201-restricted T cell responses at days 10 or 180 after immunization. For protection assays, animals were vaccinated once with 0.1-0.5 ml virus vaccine given by intramuscular or intraperitoneal route. Three weeks or six months after immunization, animals were anesthetized, infected intranasally with *vaccinia* virus Western Reserve diluted in 30 µl phosphate buffered saline, and monitored for at least further three weeks for morbidity and mortality with daily measurement of individual body weights and scoring of signs of illness as described previously. Animals suffering from severe systemic infection and having lost >30% of body weight were sacrificed. The mean change in body weight was calculated as the percentage of the mean weight for each group on the day of challenge. Body temperature was determined with a Electronic Laboratory Animal Monitoring System (BioMedic Data Systems, Marywood, N.J.) using subcutaneously implanted microchip battery-free transponders and a DAS-5004 Pocket Scanner for data collection. Mean changes in body temperatures were calculated by subtracting the pre-challenge (days –3 to 0) baseline temperature of each group from each subsequent time point.

Results

Deletion of IL1βR coding sequences from the MVA genome. In order to analyze the possible role of IL1βR gene expression during MVA infection, we constructed MVA knock-out mutants lacking the open reading frame (ORF) 184R (IL1βR). The coding sequences of the viral IL1βR together with its presumed promoter sequence are well conserved within the MVA genome. Equal to the previously characterized IL1βR of *vaccinia* virus strain Western Reserve the predicted MVA polypeptide consists of 326 amino acids at an identity level of 99% (2, 5, 34). Using PCR, we amplified DNA segments located up- and downstream of the 184R coding sequence and inserted these fragments into the deletion vector pΔK1L (FIG. 1), which contains the *vaccinia* virus K1L gene as selectable marker. Upon transfection of MVA infected cells with pΔK1L-184R, the 184R-flanking regions allowed for introduction of the K1L marker gene and simultaneous deletion of the IL1βR gene sequence in the MVA genome by homologous recombination. The resulting viruses were selected on RK-13 cells, where K1L function is essential for MVA growth. After isolation of clonally pure mutant viruses the K1L marker cassette was removed upon passage on CEF cells yielding the final mutant viruses MVA-ΔIL1βR (FIG. 1).

Molecular characterization and unimpaired in vitro replication of mutant virus MVA-ΔIL1βR. After isolation of the MVA deletion mutants we first wished to confirm the correct removal of IL1βR coding sequences on a genetic level. We analyzed viral DANN extracted from CEF cells infected with wild-type or mutant MVA by PCR using oligonucleotide primers specific for MVA genomic sequences adjacent to the IL1βR gene locus. This PCR specifically amplified 2.1-kb DNA fragments from wild-type MVA templates, whereas the use of DNA from MVA-ΔIL1βR-infected cells generated 1.1-kb PCR products corresponding to the expected reduction of molecular weights after deletion of ORF 184R (FIG. 2A). Furthermore, we digested viral DNAs with restriction endonuclease EcoRI and revealed DNA fragments containing the IL1βR gene locus by Southern blot analysis. Confirming the PCR data, we detected an about 1.3-kb lower molecular weight EcoRI-fragment in the genomic DNA of deletion mutant MVA-ΔIL1βR (FIG. 2B) again confirming the proper deletion of the targeted ORF 184R sequences. In a second step we wanted to prove that IL1βR protein is produced during MVA infection and to demonstrate that the generated mutants fail to synthesize this polypeptide. Therefore, we performed immunoprecipitation experiments with polyclonal IL1βR-specific antibodies using lysates of metabolically labeled CEF cells infected with MVA or MVA-ΔIL1βR (FIG. 2C). The antiserum precipitated a specific protein of about 45 kDa from cell lysates obtained after infection with wild-type MVA corresponding in size to the glycosylated product of the IL-1βR polypeptide found in *vaccinia* virus WR infected cells (2). In contrast, this protein was not detected in lysates from mock infected or MVA-16 ΔIL1βR-infected cells demonstrating that the generated deletion mutant virus failed to make an IL1βR product. Furthermore, we wanted to asses the replicative capacity of mutant MVA-ΔIL1βR in comparison to wild-type MVA. After infections of CEF we found very comparable amounts of new viral progeny being formed at nearly identical kinetics during one step (FIG. 2D) and multiple step (FIG. 2E) virus growth. This data clearly suggested that inactivation of MVA ORF 184R does not affect the in vitro multiplication of the virus.

Avirulence of MVA-ΔIL1βR upon high dose respiratory infection of mice. An important question was whether the inability to produce the viral IL-1βR protein would influence the outcome of MVA infection in vivo. Previous work in mice with *vaccinia* virus WR deletion mutants had revealed either enhancement of respiratory disease after intranasal infection (2) or reduced virulence after intracranial infection (34). The more severe respiratory infection appears to be linked to induction of fever response and the functional activity of the viral IL-1βR neutralizing IL-1β as major endogenous pyrogen (3). Therefore, we tested mutant virus MVA-ΔIL1βR upon intranasal infection of mice. Severity of disease in this mouse model is well reflected by changes in body weight and appearance of characteristic signs of illness (3, 12, 28, 29, 43). Additionally, we wished to monitor for changes in body temperatures because of the possible onset of febrile reactions. We transplanted BALB/c mice with subcutaneous microchip transponders to allow for computable readings, one week later infected the animals with 108 IU of MVA or MVA-ΔIL1βR or with 5×10$^5$ PFU of replication competent *vaccinia* virus CVA or 3×10$^4$ PFU Western Reserve (WR) as control, and monitored animals daily over a period of three weeks (FIG. 3). Infection of mice with MVA or mutant MVA-ΔIL1βR did not result in any obvious disease. In contrast infection with replication competent viruses CVA and WR caused drastic loss of body weight (FIG. 3A) and severe signs of illness being also well reflected by reduced body temperature (FIG. 3B). In MVA infected animals, body temperature remained stable over the observation period. Taken together, these data suggested preservation of the attenuated phenotype of MVA after deletion of the IL1βR gene from its genome.

Figure 4:
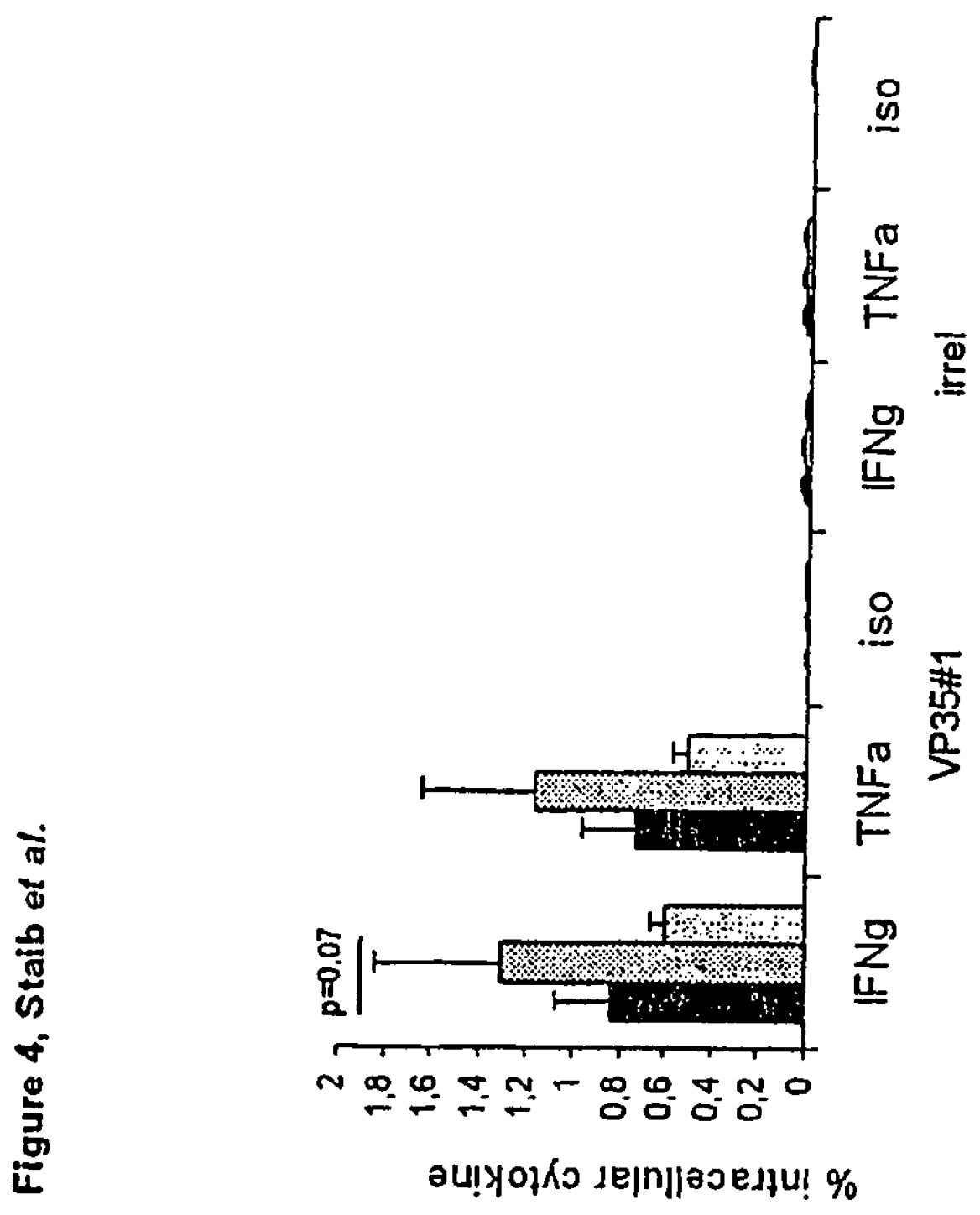

Early immune response induced by vaccination with MVA-ΔIL1βR. It was of particular interest to assess, what possible influence deletion of the immunomodulatory IL1βR gene may have on MVA immunogenicity. First, we vaccinated HLA-A*0201 transgenic mice with a single dose of MVA or deletion mutant and monitored directly ex vivo in the acute phase of the immune response for induction of vaccinia virus-specific CD8+ T-cell responses using the orthopoxvirus specific HLA-A*0201 restricted peptide epitope VP35#1 (12). By FACS analysis of freshly prepared splenocytes from vaccinated animals we were able to detect 0.4 to 2.45% of activated CD8+ T cells after immunization with MVA-ΔIL1βR, whereas in animals inoculated with MVA levels of IFNγ releasing CD8+ T cells range from 0.16 to 0.82%. We analyzed 12 individual mice per group for VP35#1 specific T cell induction, including also a group vaccinated with revertant virus MVA-IL1βRev. FIG. 4 depicts a difference between the groups of vaccinees, which albeit not statistically significant showed a tendency towards significance (p=0.07) with regard to higher levels of T cell immunogenicity elicited by MVA-ΔIL1βR. Importantly, vaccinations with the revertant virus MVA-IL1βRev resulted in T cell responses that were very comparable to those induced by MVA wildtype.

Protective capacity of MVA-ΔIL1βR immunization. Having found slightly higher VP35#1 epitope-specific CD8+ T cell responses after immunization with MVA-ΔIL1βR mutant virus, we wished to ascertain possible differences in protective capacity of MVA and the MVA deletion mutant. For this we used a recently established mouse model, where groups of mice are vaccinated once intramuscularly with different doses of MVA vaccine, followed by a lethal intranasal challenge with vaccinia virus WR at three weeks after immunization (FIG. 5) (12). Body weight (FIG. 5A, B) and signs of illness (FIG. 5C, D) of animals were monitored daily for a period of three weeks after the challenge. Vaccination with both MVA vaccines given at $10^5$ or higher doses fully protected all mice, whereas $10^4$ or less resulted in death of all animals. This model has the advantage, that the observed vaccine protection titrates with the dose administered being depicted by the changes in average body weights of the various groups. Here by, we determined very similar weight curves for the different groups of mice immunized with MVA or MVA-ΔIL1βR vaccines (FIG. 5A, B). This result was further confirmed when we monitored for the typical signs of illness after infection (FIG. 5C, D), as with increasing vaccine dose, signs of illness decreased alike among corresponding groups. Thus, MVA and MVA-ΔIL1βR showed a very comparable capacity to elicit protective responses within three weeks after vaccination being in agreement with our finding of similar acute phase immune responses.

MVA-ΔIL1βR vaccination improves T cell memory response and long-term protective capacity. The mature form of the inflammatory cytokine IL1β has multiple effects in vivo as revealed by the study of mice deficient for different components of the IL-1 system (33). An active area of ongoing research on IL1 function is to elucidate the likely importance of the cytokine in protective T cell immunity including the activation of professional antigen presenting cells and memory T cells (16, 17). To investigate whether the inactivation of viral IL1βR influences the formation of memory T cell responses, we vaccinated groups of HLA-A*0201 transgenic (HHD) mice once with $10^8$ IU MVA-ΔIL1βR or MVA and monitored for virus-specific T cells more than six months after this primary immunization. At late times after vaccination relatively low levels of VP35#1-specific memory T cells can be detected using our standard protocol for ICS/FACS analysis (0.30-0.60%) (11). An improved protocol using overnight incubation of peptide stimulated splenocytes allows to notice a more prominent population of antigen-specific CD8+ T cells often exceeding the number of activated T cells found with our conventional protocol during the acute phase response. Here by, we detected clearly higher levels (up to 5.8%) of VP35#1-reactive and IFN-γ releasing splenic CD8+ memory T cells in MVA-ΔIL1βR immunized animals as compared to vaccination with non recombinant MVA resulting in up to 1.6% epitope-specific IFN-γ-secreting CD8+ T cells (FIG. 6A). This difference in favour of MVA-ΔIL1βR vaccination was statistically significant (p=0.01), and, interestingly, splenocytes from vaccinees of this group also contained higher amounts of total vaccinia-specific CD8+ memory T cells, while we found comparable average levels of CD4+ T cells for both MVA-ΔIL1βR and MVA. To monitor if the different levels of memory T cell responses would go along with alterations in protection, we challenged HHD mice by intranasal inoculation of $10^7$ PFU vaccinia virus Western Reserve after being vaccinated with a single intraperitoneal inoculation of $10^8$ IU MVA-ΔIL1βR or MVA more than six months earlier (FIG. 6B). The infection resulted in mock vaccinated control animals in the onset of respiratory disease, weight loss, and death within 8 days after challenge. Mice inoculated with wildtype MVA were also affected by respiratory illness and substantial loss of body weight. Yet, the animals were partially protected because 3 out of 5 mice in this group survived the challenge infection. Notably, all animals (5/5) receiving the MVA-ΔIL1βR vaccine were protected, an outcome that was also well reflected with regard to the lesser extent of weight loss and illness observed in this group (data not shown). This result implied that vaccination with MVA-ΔIL1βR could indeed have an influence on the durability of protective immunity. The HHD mouse model allows for convenient analysis of epitope specific HLA-A*0201-restricted CD8+ T cell responses, yet, possibly because of their knock-out phenotype for mouse MHC class I, these mice develop unusually low numbers of total CD8+ T cells (but normal levels of CD4+ T cells) (11). As this phenotype might influence the analysis of total vaccinia-specific T cell responses, we assessed total CD8+ memory T cells induced by MVA-ΔIL1βR or MVA also after vaccination of normal C57BL/6 mice (FIG. 7A). Again in comparison to conventional MVA vaccination we found significantly (p=0.001) higher numbers of vaccinia-specific CD8+ T cells in animals immunized with MVA-ΔIL1βR. This data strongly suggested an improved capacity of MVA-ΔIL1βR to elicit or maintain vaccinia virus-specific CD8+ T cell memory. To investigate the longterm efficacy of MVA-ΔIL1βR immunization in more detail, we decided to test the vaccines also in the well established challenge model using non transgenic BALB/c mice (5, 11). We chose intranasal vaccination as this route of MVA immunization of mice results in comparison to intramuscular or intraperitoneal vaccination in lower levels of circulating virus-specific antibodies, which might be an advantage when assessing the potential protective capacity of T cell immunity. We inoculated groups of BALB/c mice with $10^5$ to $10^7$ IU of MVA-ΔIL1βR or MVA. Four months after immunization, we submitted animals again to a respiratory infection with $10^7$ PFU of vaccinia virus Western Reserve (FIG. 7B). Importantly, all mice having received MVA-ΔIL1βR vaccine survived the challenge, and animals in the group vaccinated with $10^7$ IU of MVA-ΔIL1βR demonstrated an average <15% reduction of body weight and only mild signs of illness (data not shown). In contrast, no protection from severe disease resulting in death of all animals was seen after inoculation with $10^5$ IU MVA vaccine (Fisher exact test p=0.029), and while vaccination with higher doses ($10^6$, $10^7$ IU) of MVA prevented death, animals in these groups showed a ≧20% average weight loss and enhanced signs of disease (data not shown).

The MVA ORF 184R encodes a *vaccinia* viral soluble receptor for IL-1β with proposed function to block inflammatory and febrile host response to infection. The removal of putative immune evasion genes from viral genomes is a promising approach to further elucidate roles of these regulatory virus proteins in the in vivo viral life cycle (1). Moreover, application of this research to a virus such as MVA being suitable for use as (recombinant) live viral vaccine may directly lead to second generation vaccines with rationally improved properties. Even by means of molecular engineering techniques allowing for precise mutagenesis (35, 36) the resulting phenotypes of mutant viruses are unpredictable, and the inactivation of the MVA IL1βR gene may serve as further example. Our finding that inactivation of the 184R ORF had no impact on the in vitro replicative capacity of the MVA mutant virus can be considered as quite unsurprising because no growth deficiencies have been reported with corresponding mutants derived from *vaccinia* virus WR (2). Yet, capacity for high level amplification is of utmost importance for a virus possibly serving in vaccine production. Additionally, it should be noted that with another MVA mutant defective in expression of the viral interferon response gene E3L we had recently found a very unexpected host range phenotype in CEF the preferred cell culture for MVA vaccine production (15). Of course, it was even more interesting to investigate the in vivo properties of MVA-ΔIL1βR. It was possible that an unhampered IL1β activity elicited by infection with MVA-ΔIL1βR would trigger strong inflammation reactions and febrile responses that result in adverse effects of vaccination. In a more optimistic scenario we speculated that IL1β action could be locally restricted and might influence the potency of MVA immunization in an adjuvant-like manner. Upon intranasal infection of BALB/c mice with MVA-ΔIL1βR we did not detect signs of respiratory illness despite using high dose inoculations and despite the fact that this mouse model system appears to be particularly suitable to assess potential pathogenic consequences of inflammatory responses to viral infection (3, 28, 30). Our inability to detect pathogenic effects after infection with MVA-ΔIL1βR might be a consequence of the particular MVA genotype with other *vaccinia* virus regulatory or immunomodulatory genes being fragmented or deleted (5). Yet, alternatively it could likely be that the disease enhancement observed with *vaccinia* virus IL1βR-deletion mutants requires active in vivo replication of the virus after intranasal infection. As there is good recent evidence confirming that MVA is incapable to productively replicate in vivo in mice (27) or macaques (39), our data might suggest that transient one-step infection with MVA-ΔIL1βR is just not sufficient to result in IL1β, activities inducing adverse systemic fever or inflammation reactions. In first vaccination experiments we found equal properties of MVA and MVA-ΔIL1βR with regard to vaccine immunogenicity monitoring for early total anti-*vaccinia* virus antibody or T cell responses. Data that was well confirmed by the close to identical capacity of both viruses to protect animals from lethal *vaccinia* virus challenge given three weeks after vaccination.

Of particular interest is our demonstration of the benefit of MVA-ΔIL1βR immunization when monitoring for *vaccinia* virus epitope-specific T cell responses. The H3L gene product-derived epitope VP35#1 is the target of an immunodominant HLA-A*0201-restricted T cell specificity and can be used to examine the induction of virus-specific CD8+ T cells in an epitope-specific manner (10, 12). In contrast, bulk analysis of total *vaccinia* virus-specific responses offers a representative picture based on a multitude of different T cell specificities but might not allow to assess subtle changes in the activation of single T cell populations. Suspecting a possible effect on T cell activation we opted to also assess VP35#1-specific T cell memory responses which we had previously found detectable for more than 6 month after vaccination of HLA-A*0201 transgenic mice (12). Indeed, we observed a clearly more prominent enhancement of VP35#1-specific T cell responses after vaccination with MVA-ΔIL1βR (p=0.01). Moreover, our additional findings appeared to solidly confirm a longterm beneficial effect of MVA-ΔIL1βR immunization. We had noticed for the first time an increased total CD8+ T cell responses in transgenic HHD mice, and more importantly, we observed significantly enhanced total CD8+ T cells after vaccination of non-transgenic C57BL/6 mice (p=0.001). In addition, we found higher protective capacities against lethal respiratory challenge with *vaccinia* virus Western Reserve in both HLA-A*0201 transgenic mice and normal BALB/c mice. How to explain an enhanced vaccine efficacy in the context of IL1β function? Interestingly, results from two recent studies investigating the Leishmania major infection of susceptible or resistant mice suggest that the ability of dendritic cells (DC) to secrete IL1α or IL1β is specifically associated with the induction of protective Th1 immunity (13, 42). In addition, there is recent evidence for IL1β being an essential mediator of Fas-ligation induced maturation of murine DC (14). The same work demonstrated that maturation of murine DC could be completely abrogated by the use of IL1β neutralizing antibodies which may function in a similar manner as one could expect with the soluble *vaccinia* virus IL1βR molecule. Therefore, the lack of IL1β neutralization upon vaccination with MVA-ΔIL1βR may lead to improved functionality of DC to serve as antigen-presenting cells, which might result in better T cell memory responses. Similarly, it has been shown that stimulation of endothelial cells with IL1β resulted in ICOS-L mediated activation of memory T cells (17). Such activity of IL1β might be the functional basis for our finding that vaccination with MVA-ΔIL1βR appeared to predominantly improve memory T cell responses. In addition, at early times after immunization, we did not find differences in the in vivo protective capacity of MVA wildtype or mutant vaccines. This may also indicate that the viral IL1βR could have a specific role in abrogating anti-viral memory T cell responses. Alternatively, we might have been unable to detect a more general effect of the viral IL1βR expression on virus-specific T cell immunity upon early ex vivo analysis at what likely is the peak level of vaccine induced T cell response, and our inability to demonstrate differences in protective capacities could be due to the impact of high level antibody mediated immunity during early weeks after immunization. The important role of virus-specific antibodies to protect against a lethal respiratory challenge with virulent *vaccinia* virus has been clearly demonstrated (6), yet the completely protective MVA vaccination in B cell deficient mice suggests that T cell immunity may complement for the lack of *vaccinia* virus-specific antibody responses (44). The capacity of the viral IL1βR to apparently specifically downmodulate anti-viral CD8+ T cell memory responses appears alluring in the view of recent data from the analysis of *vaccinia* virus-specific memory T cells in humans (after vaccination with conventional wildtype *vaccinia* virus) showing better persistence of CD4+ than CD8+ T cells (4). In summary, our analysis recommends deletion of the viral IL1βR gene as a first step in approaching the development of a new generation of MVA-based vaccines. High virus titers could be obtained upon in vitro propagation of deletion mutant MVA-ΔIL1βR, and there was no evidence of MVA-ΔIL1βR being less well tolerated than wildtype virus upon high dose in vivo infection. Our finding of improved vaccine properties of MVA-ΔIL1βR is particularly. promising because it provides first evidence for the possibility of obtaining more efficacious MVA vaccines through rational genetic engineering.

REFERENCES

1. Alcami, A. 2003. Viral mimicry of cytokines, chemokines and their receptors. Nat Rev Immunol 3:36-50.
2. Alcami, A., and G. Smith. 1992. A soluble receptor for Interleukin-1b encoded by *vaccinia* virus: a novel mechanism of virus modulation of the host response to infection. Cell 71:153-167.
3. Alcami, A., and G. L. Smith. 1996. A mechanism for the inhibition of fever by a virus. Proc Natl Acad Sci USA 93:11029-11034.
4. Amara, R., P. Nigam, S. Sharma, J. Liu, and V. Bostik. 2004. Long-lived poxvirus immunity, robust CD4 help, and better persistence of CD4 than CD8 T cells. J Virol 78:3811-6.
5. Antoine, G., F. Scheiflinger, F. Dorner, and F. G. Falkner. 1998. The complete genomic sequence of the modified *vaccinia* Ankara strain: comparison with other orthopoxviruses. Virology 244:365-96.
6. Belyakov, I. M., P. Earl, A. Dzutsev, V. A. Kuznetsov, M. Lemon, L. S. Wyatt, J. T. Snyder, J. D. Ahlers, G. Franchini, B. Moss, and J. A. Berzofsky. 2003.
Shared modes of protection against poxvirus infection by attenuated and conventional smallpox vaccine viruses. Proc Natl Acad Sci U S A 100:9458-63.
7. Carroll, M. W., and B. Moss. 1997. Host range and cytopathogenicity of the highly attenuated MVA strain of *vaccinia* virus: propagation and generation of recombinant viruses in a nonhuman mammalian cell line. Virology 238: 198-211.
8. Corona Gutierrez, C. M., A. Tinoco, M. Lopez Contreras, T. Navarro, P. Calzado, L. Vargas, L. Reyes, R. Posternak, and R. Rosales. 2002. Clinical protocol. A phase II study: efficacy of the gene therapy of the MVA E2 recombinant virus in the treatment of precancerous lesions (NIC I and NIC II) associated with infection of oncogenic human papillomavirus. Hum Gene Ther 13:1127-40.3
9. Cosma, A., R. Nagaraj, S. Buhler, J. Hinkula, D. H. Busch, G. Sutter, F. D. Goebel, and V. Erfle. 2003. Therapeutic vaccination with MVA-HIV-1 nef elicits Nef-specific T-helper cell responses in chronically HIV-1 infected individuals. Vaccine 22:21-9.
10. Di Nicola, M., C. Carlo-Stella, A. Anichini, R. Mortarini, A. Guidetti, G. Tragni, F. Gallino, M. Del Vecchio, F. Ravagnani, D. Morelli, P. Chaplin, N. Arndtz, G. Sutter, I. Drexler, G. Parmiani, N. Cascinelli, and A. M. Gianni. 2003. Clinical protocol. Immunization of patients with malignant melanoma with autologous CD34(+) cell-derived dendritic cells transduced ex vivo with a recombinant replication-deficient *vaccinia* vector encoding the human tyrosinase gene: a phase I trial. Hum Gene Ther 14:1347-60.
11. Drexler, I., K. Heller, B. Wahren, V. Erfle, and G. Sutter. 1998. Highly attenuated modified *vaccinia* virus Ankara replicates in baby hamster kidney cells, a potential host for virus propagation, but not in various human transformed and primary cells. J Gen Virol 79:347-352.
12. Drexler, I., C. Staib, W. Kastenmuller, S. Stevanovic, B. Schmidt, F. A. Lemonnier, H. G. Rammensee, D. H. Busch, H. Bernhard, V. Erfle, and G. Sutter. 2003. Identification of *vaccinia* virus epitope-specific HLA-A*0201-restricted T cells and comparative analysis of smallpox vaccines. Proc Natl Acad Sci U S A 100:217-222.
13. Filippi, C., S. Hugues, J. Cazareth, V. Julia, N. Glaichenhaus, and S. Ugolini. 2003. CD4+ T cell polarization in mice is modulated by strain-specific major histocompatibility complex-independent differences within dendritic cells. J Exp Med 198:201-9.
14. Guo, Z., M. Zhang, H. An, W. Chen, S. Liu, J. Guo, Y. Yu, and X. Cao. 2003. Fas ligation induces IL-1beta-dependent maturation and IL-1beta-independent survival of dendritic cells: different roles of ERK and NF-kappaB signaling pathways. Blood 102:4441-7.
15. Hornemann, S., O. Harlin, C. Staib, S. Kisling, V. Erfle, B. Kaspers, G. Hacker, and G. Sutter. 2003. Replication of modified *vaccinia* virus Ankara in primary chicken embryo fibroblasts requires expression of the interferon resistance gene E3L. J Virol 77:8394-407.
16. Iwasaki, A. 2003. The importance of CD11b+ dendritic cells in CD4+ T cell activation in vivo: with help from interleukin 1. J Exp Med 198:185-90.
17. Khayyamian, S., A. Hutloff, K. Buhner, M. Grafe, V. Henn, R. A. Kroczek, and H. W. Mages. 2002. ICOS-ligand, expressed on human endothelial cells, costimulates Th1 and Th2 cytokine secretion by memory CD4+ T cells. Proc Natl Acad Sci U S A 99:6198-203.
18. Mayr, A., V. Hochstein-Mintzel, and H. Stickl. 1975. Abstammung, Eigenschaften und Verwendung des attenuierten *Vaccinia*-Stammes MVA. Infection 3:6-14.
19. Mayr, A., and E. Munz. 1964. Veranderungen von Vaccinevirus durch Dauerpassagen in Hühnerfibroblastenkulturen. Zbl. Bakt. I. Abt. Orig. 195:24.
20. Mayr, A., H. Stickl, H. Müller, K. Danner, and H. Singer. 1978. Der Pockenimpfstamm MVA: Marker, genetische Struktur, Erfahrungen mit der parenteralen Schutzimpfung und Verhalten im abwehrgeschwächten Organismus. Zbl. Bakt. Hyg., I.Abt. Orig. B 167:375-390.
21. McConkey, S. J., W. H. Reece, V. S. Moorthy, D. Webster, S. Dunachie, G. Butcher, J. M. Vuola, T. J. Blanchard, P. Gothard, K. Watkins, C. M. Hannan, S. Everaere, K. Brown, K. E. Kester, J. Cummings, J. Williams, D. G. Heppner, A. Pathan, K. Flanagan, N. Arulanantham, M. T. Roberts, M. Roy, G. L. Smith, J. Schneider, T. Peto, R. E. Sinden, S. C. Gilbert, and A. V. Hill. 2003. Enhanced T-cell immunogenicity of plasmid DNA vaccines boosted by recombinant modified *vaccinia* virus Ankara in humans. Nat Med 9:729-35.
22. Meyer, H., G. Sutter, and A. Mayr. 1991. Mapping of deletions in the genome of the highly attenuated *vaccinia* virus MVA and their influence on virulence. J Gen Virol 72:1031-1038.
23. Moss, B., M. W. Carroll, L. S. Wyatt, J. R. Bennink, V. M. Hirsch, S. Goldstein,
W. R. Elkins, T. R. Fuerst, J. D. Lifson, M. Piatak, N. P. Restifo, W. Overwijk, R. Chamberlain, S. A. Rosenberg, and G. Sutter. 1996. Host range restricted, non-replicating *vaccinia* virus vectors as vaccine candidates. Adv Exp Med Biol 397:7-13.

24. Moss, B., and P. L. Earl. 1991. Preparation of cell cultures and *vaccinia* virus stocks, p. 16.16.1-16.16.7. In F. M. Ausubel, R. Brent, R. Kingston, D. Moore, J. Seidman, J. Smith, and K. Struhl (ed.), Current Protocols in Molecular Biology. John Wiley & Sons, New York.

25. Moss, B., and J. L. Shisler. 2001. Immunology 101 at poxvirus U: Immune evasion genes. Semin Immunol 13:59-66.

26. Pascolo, S., N. Bervas, J. M. Ure, A. G. Smith, F. A. Lemonnier, and B. Perarnau. 1997. HLA-A2.1-restricted education and cytolytic activity of CD8(+) T lymphocytes from beta2 microglobulin (beta2m) HLA-A2.1 monochain transgenic H-2Db beta2m double knockout mice. J Exp Med 185:2043-51.

27. Ramirez, J. C., M. M. Gherardi, and M. Esteban. 2000. Biology of attenuated modified *vaccinia* virus Ankara recombinant vector in mice: virus fate and activation of B- and T-cell immune responses in comparison with the Western Reserve strain and advantages as a vaccine. J Virol 74:923-33.

28. Reading, P. C., J. B. Moore, and G. L. Smith. 2003. Steroid hormone synthesis by *vaccinia* virus suppresses the inflammatory response to infection. J Exp Med 197:1269-78.

29. Reading, P. C., and G. L. Smith. 2003. A kinetic analysis of immune mediators in the lungs of mice infected with *vaccinia* virus and comparison with intradermal infection. J Gen Virol 84:1973-83.

30. Reading, P. C., and G. L. Smith. 2003. *Vaccinia* virus interleukin-18-binding protein promotes virulence by reducing gamma interferon production and natural killer and T-cell activity. J Virol 77:9960-8.

31. Rochlitz, C., R. Figlin, P. Squiban, M. Salzberg, M. Pless, R. Herrmann, E. Tartour, Y. Zhao, N. Bizouarne, M. Baudin, and B. Acres. 2003. Phase I immunotherapy with a modified *vaccinia* virus (MVA) expressing human MUC1 as antigen-specific immunotherapy in patients with MUC1-positive advanced cancer. J Gene Med 5:690-9.

32. Sambrook, J., E. F. Fritsch, and T. Maniatis. 1989. Molecular cloning: A laboratory manual, 2 ed. Cold Spring Harbor Laboratory Press, Cold Spring Harbor New York.

33. Sims, J. E. 2002. IL-1 and IL-18 receptors, and their extended family. Curr Opin Immunol 14:117-22.

34. Spriggs, M., D. Hruby, C. Maliszewski, D. Pickup, J. Sims, R. Buller, and J. VanSlyke. 1992. *Vaccinia* and cowpox viruses encode a novel secreted interleukin-1-binding protein. Cell 71:145-152.

35. Staib, C., I. Drexler, M. Ohlmann, S. Wintersperger, V. Erfle, and G. Sutter. 2000. Transient host range selection for genetic engineering of modified *vaccinia* virus Ankara [In Process Citation]. Biotechniques 28:1137-42, 1144-6, 1148.

36. Staib, C., M. Lowel, V. Erfle, and G. Sutter. 2003. Improved host range selection for recombinant modified *vaccinia* virus Ankara. Biotechniques 34:694-6, 698, 700.

37. Staib, C., and G. Sutter. 2003. Live viral vectors: *vaccinia* virus. Methods Mol Med 87:51-68.

38. Stickl, H., V. Hochstein-Mintzel, A. Mayr, H. Huber, H. Schafer, and A. Holzner. 1974. MVA-Stufenimpfung gegen Pocken. Dtsch. med. Wschr. 99:2386-2392.

39. Stittelaar, K. J., T. Kuiken, R. L. de Swart, G. van Amerongen, H. W. Vos, H. G. Niesters, P. van Schalkwijk, T. van der Kwast, L. S. Wyatt, B. Moss, and A. D. Osterhaus. 2001. Safety of modified *vaccinia* virus Ankara (MVA) in immune-suppressed macaques. Vaccine 19:3700-9.

40. Sutter, G., and B. Moss. 1992. Nonreplicating *vaccinia* vector efficiently expresses recombinant genes. Proc Natl Acad Sci USA 89:10847-10851.

41. Sutter, G., and B. Moss. 1995. Novel *vaccinia* vector derived from the host range restricted and highly attenuated MVA strain of *vaccinia* virus. Dev Biol Stand 84:195-200.

42. Von Stebut, E., J. M. Ehrchen, Y. Belkaid, S. L. Kostka, K. Molle, J. Knop, C. Sunderkotter, and M. C. Udey. 2003. Interleukin 1alpha promotes Th1 differentiation and inhibits disease progression in Leishmania major-susceptible BALB/c mice. J Exp Med 198:191-9.

43. Williamson, J. D., R. W. Reith, L. J. Jeffrey, J. R. Arrand, and M. Mackett. 1990. Biological characterization of recombinant *vaccinia* viruses in mice infected by the respiratory route. J Gen Virol 71:2761-7.

44. Wyatt, L. S., P. L. Earl, L. A. Eller, and B. Moss. 2004. Highly attenuated smallpox vaccine protects mice with and without immune deficiencies against pathogenic *vaccinia* virus challenge. Proc Natl Acad Sci U S A 101:4590-5.

What is claimed is:

1. A MVA mutant, wherein the IL1βR coding sequence or a part thereof has been inactivated for use in immunotherapy and/or vaccination, wherein the MVA mutant further comprises DNA sequences coding for a heterologous protein derived from the group consisting of therapeutic polypeptides and polypeptides of pathogenic agents and functional parts thereof, wherein the MVA mutant leads to enhanced memory response of CD8+ cells of at least 10% compared to wild type MVA.

2. The MVA mutant of claim 1, wherein the therapeutic polypeptide is derived from the group consisting of polypeptides, antibodies, chemokines, cytokines, interferons, and other secreted polypeptides.

3. The MVA mutant of claim 1, wherein the pathogenic agent is derived from the group consisting of viruses, bacteria, protozoa, parasites, tumor cells or tumor cell associated antigens and functional parts thereof.

4. The MVA mutant of claim 3, wherein the viruses are selected from the group consisting of influenza viruses, measles, respiratory syncytial viruses, dengue viruses, human immunodeficiency viruses, human hepatitis viruses, herpes viruses, and papilloma viruses.

5. The MVA mutant of claim 3, wherein the protozoa is *Plasmodium falciparum*.

6. The MVA mutant of claim 3, wherein the bacteria is tuberculosis-causing Mycobacteria.

7. The MVA mutant of claim 3, wherein the tumor cell associated antigen is selected from the group consisting of tyrosinase, tyrosinase-related proteins 1 and 2, other melanoma-associated differentiation antigens, MAGE-1, MAGE-2, MAGE-3, and BAGE, other cancer testes antigens, and non-mutated shared antigens overexpressed on tumors.

8. A pharmaceutical composition comprising one or more of the MVA mutants of any one of claims 1 and 2-7 and a pharmaceutically acceptable carrier.

9. The pharmaceutical composition of claim 8, which is adapted for in vivo use in a mammal.

10. A method of generating mutant MVA, comprising the steps of:
   Infecting host cells of MVA with a nucleic acid coding for the MVA mutants of any of claims 1 and 2-7;
   expressing said nucleic acid under suitable conditions in said host cells; and
   isolating expressed mutant MVA.

11. A method for generating a pharmaceutical composition comprising the steps of:

Infecting host cells of MVA with a nucleic acid coding for the MVA mutants of any of claims 1 and 2-7;

expressing said nucleic acid under suitable conditions in said host cells;

isolating expressed mutant MVA; and adding a pharmaceutically acceptable carrier and further ingredients in order to manufacture a pharmaceutical composition.

12. The method of claim 10 wherein the host cells are CEF cells, chicken embryo derived LSCC-H32 cells, chicken DF-1 cells, quail fibroblasts QT6, quail fibroblasts QT35 cells or other avian cells.

13. The method of claim 10 wherein the mutant MVA are selected by the K1L gene-based host range selection protocol.

14. The pharmaceutical composition of claim 9, wherein the mammal is a human.

15. The MVA mutant of claim 1, wherein the IL1βR coding sequence is inactivated by deletion or mutation.

* * * * *

UNITED STATES PATENT AND TRADEMARK OFFICE
CERTIFICATE OF CORRECTION

PATENT NO.        : 7,767,209 B2  
APPLICATION NO.   : 11/375159  
DATED             : August 3, 2010  
INVENTOR(S)       : Staib et al.

Page 1 of 1

It is certified that error appears in the above-identified patent and that said Letters Patent is hereby corrected as shown below:

On title page, item 73 Assignee  
      replace "GSF-Forschungszentrum fuer Umwelt und Gesundheit GmbH, Munich (DE)"  
      with --"Helmholtz Zentrum München Deutsches Forschungszentrum für Gesundheit  
          und Umwelt (GmbH), Munich (DE)"--.

Signed and Sealed this  
Nineteenth Day of July, 2011

David J. Kappos  
*Director of the United States Patent and Trademark Office*